United States Patent [19]

Rotbart

[11] Patent Number: 5,075,212
[45] Date of Patent: Dec. 24, 1991

[54] METHODS OF DETECTING PICORNAVIRUSES IN BIOLOGICAL FLUIDS AND TISSUES

[75] Inventor: Harley A. Rotbart, Denver, Colo.

[73] Assignee: University of Patents, Inc., Westport, Conn.

[21] Appl. No.: 329,428

[22] Filed: Mar. 27, 1989

[51] Int. Cl.$^5$ .................. C12G 1/70; C12P 11/58; C12N 11/62
[52] U.S. Cl. .......................... 435/5; 435/77; 435/172.3; 536/27
[58] Field of Search ................ 435/91, 5, 177.3

[56] References Cited

U.S. PATENT DOCUMENTS 4,683,195  7/1987  Mullis .
4,683,202  7/1987  Mullis ........................... 435/91

OTHER PUBLICATIONS

Rotbart et al., J. Clin. Microbiol. 20:1105–1108, (1984).
Rotbart et al., J. Clin, Microbiol 22:220–224, (1985).
Rotbart and Levin, Chapter 15, "Progress Toward the Development of a Pan-Enteroviral Nucleic Acid Probe", in DNA Probes for Infectious Diseases, pp. 193-209, 197.
Rotbart et al., Molecular and Cellular Probes 2:65–73, (1988).
Eur. J. Immunol. vol. 18, issued 1988 Brueggemann et al., "Sequence of a Rat Immunoglobulin $\gamma 2_c$ Heavy Chain Constant Region cDNA: Extensive Homology to Mouse $\gamma_3$".
FEBS Lett., vol. 192; issued 1985, Chong, et al., "Structural Analysis of a New GC Specific Insertion Element IS186".
Virology, vol. 156, issued 1987, Iizuka et al., "Complete Nucleotide Sequence of the Genome of Coxsackievirus B1".
Journal of Clinical Microbiology, issued Dec. 1988, Rotbart et al., "Nonisotopic Oligomeric Probes for the Human Enteroviruses".
Orkin, Stuart H., "Genetic Diagnosis by DNA Analysis", The New England Journal of Medicine, vol. 317, No. 16, pp. 1023-1025.
Schochetman, G. et al., "Polymerase Chain Reaction", The Journal of Infectious Diseases, vol. 158, No. 6, Dec. 1988, pp. 1154-1157.
Saiki, R. K. et al., "Primer-Directed Enzymatic Amplification of DNA with a Thermostable DNA Polymerase", Science Reports, vol. 239, Jan. 29, 1988, pp. 487-491.
Abbott, M. A. et al., "Enzymatic Gene Amplification: Qualitative and Quantitative Methods for Detecting Proviral DNA Amplified in Vitro", The Journal of Infectious Diseases, vol. 158, No. 6, Dec. 1988, pp. 1158-1166.
Mullis, K. B. et al., "Specific Synthesis of DNA in Vitro Via A Polymerase Catalysed Chain Reaction", Methods In Enzymology, 155:335-350, 1987.
Mack, D. H. et al., "A Sensitive Method For The Identification Of Uncharacterized Viruses Related To Known Virus Groups: Hepadnavirus Model System", Proc. Natl. Acad. Sci. U.S.A., vol. 85, pp. 6977–6981, Sep. 1988.
Rigby, Peter W. J., et al., "Labeling Deoxyribonucleic Acid to High Specific Activity in vitro by Nick Translation with DNA Polymerase I", J. Mol. Biol. (1977).
Tchen, Paul, "Chemical Labeling of Nucleic Acids: An Alternative to the Use of Radioactive Isotopes", Unite de Recherches de Genetique Epidemiologique, INSERM U. 155, p. 93.
Ruth, Jerry L., "Chemical Synthesis of Non-Radioactively-Labeled DNA Hybridization Probes", Molecular Biosystems, Inc., p. 123.
Lindberg, A. Michael, et al., "Genome of Coxsackievirus B3", Virology 156, 50-63 (1987).
Denhart, David T., "A Membrane-Filter Technique for Detection of Complementary DNA", Biochemical and Biophysical Research Communications, vol. 23, No. 5, 1966.
Toyoda, Haruka, et al., "Complete Nucleotide Sequences of all Three Poliovirus Serotype Genomes; Implication For Genetic Relationship, Gene Function and Antigenic Determinants", J. Mol. Biol. (1984) 174, 561-585.
Jenkins, O., et al., "The Complete Nucleotide Sequence of Coxsackievirus B4 and Its Comparison to Other Members of the Picornaviridae", J. Gen. Virol. (1987), 68, 1835-1848.
Maniatis, T. et al., "Rapid End-labeling of DNA", Molecular Cloning (1982), pp. 117, 127.

*Primary Examiner*—Robert A. Wax
*Assistant Examiner*—Bradley L. Sisson
*Attorney, Agent, or Firm*—Woodcock Washburn Kurtz Mackiewicz & Norris

[57] ABSTRACT

The present invention discloses methods for detecting picornaviruses in biological tissues. In the methods of the invention, at least a portion of picornavirus nucleic acid present in a test sample of a biological tissue suspected of containing picornavirus is amplified. Picornavirus nucleic acid is then detected by conventional separation techniques or by hybridizing the amplified nucleic acid with at least a portion of a nucleotide probe comprising a nucleotide sequence complementary to the amplified nucleic acid and detecting the probe. The invention also provides nucleotide primers and probes having nucleotide sequences characteristic of picornaviral RNA for use in detecting the viruses.

7 Claims, No Drawings

METHODS OF DETECTING PICORNAVIRUSES IN BIOLOGICAL FLUIDS AND TISSUES

FIELD OF THE INVENTION

The present invention relates to methods of detecting viral infection of biological tissues, and more particularly to methods of detecting viral infection of biological fluids and tissues using nucleotide probes.

BACKGROUND OF THE INVENTION

The enteroviruses are a heterogeneous group of nearly 70 human pathogens which are responsible for a broad spectrum of clinical diseases. Like other members of the picornavirus family, the enteroviruses are small (27-nm), single-stranded, nonenveloped RNA viruses of approximately 1.34 g/ml buoyant density. Enteroviruses distinguish themselves from rhinoviruses, another type of human picornavirus, by their stability in acid, by their fecal-oral route of passage and transmission, and by their strict summer peak of disease activity. The prototypic enteroviruses, the polioviruses, remain the most clinically significant of the enteroviruses worldwide, causing paralytic disease in 4 of every 1,000 school-age children in developing countries. In the United States, the polioviruses have been controlled with the introduction of vaccines in the late 1950's. The nonpolio enteroviruses, however, are responsible for 5 to 10 million symptomatic infections each year. They are the most common etiologic agents of meningitis (75,000 cases per year) and of nonspecific febrile and exanthematous illnesses (5 million cases per year). They are also responsible for significant numbers of cases of myocarditis, hepatitis, pleurodynia, stomatitis, and neonatal sepsis. Recently identified nonpolio enterovirus serotypes cause hemorrhagic conjunctivitis and poliomyelitis mimicking that is due to the polioviruses. Several important diseases are suspected of having an enteroviral etiology without definitive proof; these include diabetes mellitus, dermatomyositis, congenital hydrocephalus, and amyotrophic lateral sclerosis. The enteroviruses cause infections which may persist for many years in immunocompromised individuals, often leading to death. Recently, a syndrome of late onset muscular atrophy has been reported in individuals who suffered paralytic poliomyelitis 20 to 40 years previously.

Beyond the obvious desire to determine the specific etiology of these diverse and important diseases, there are many reasons for seeking a rapid and accurate diagnostic test for the enteroviruses. It is often clinically impossible to distinguish enteroviral infections from those due to bacterial pathogens or other viruses, including herpes simplex, for which there are specific therapies. Although many enteroviral infections are self-limited and require no therapy, the fear that an illness may be bacterial or herpetic results in unnecessary hospitalization and antibiotic or antiviral treatment for thousands of enterovirus-infected patients each year. Certain enteroviral diseases are in fact severe enough to warrant specific therapy, were such available. Indeed, several experimental agents have been shown to be very effective against the enteroviruses in vitro and in animal models. These have never been studied in humans, however, because the diagnosis of enterovirus infection is currently made too slowly to conduct an appropriate clinical drug trial. Finally, as alluded to earlier, a number of diseases are theorized to be due to the enteroviruses but have not yet been proven as such. A clear association with these viruses would facilitate the understanding and treatment of such conditions.

The Nobel Prize in medicine and physiology was awarded to J. F. Enders, F. C. Robbins, and T. H. Weller in 1954 for their success in cultivating poliovirus in tissue culture, an accomplishment which paved the way for vaccine development and provided a means for laboratory testing for the polio and nonpolio enteroviruses. Since then, tissue culture continues to be the mainstay of the enteroviral diagnosis despite well-recognized limitations. Tissue culture is time-consuming and requires a high level of expertise. Of greater concern is the fact that certain of the enteroviruses will not grow in tissue culture, requiring inoculations into suckling mice for detection, a technique cumbersome enough to be omitted from almost all diagnostic laboratories. The sensitivity of routine tissue culture for the enteroviruses may be as low as 65 to 75%, and development of characteristic cytopathic effect may take too long to be of benefit to the patient. Cerebrospinal fluid (CSF) infections with the enteroviruses take a mean of 6.3 days in the laboratory for growth in culture, consistent with reported means to isolation from the CSF of 4.0 to 8.2 days. Other body sites may become positive sooner, but as meningitis is the most vexing of enteroviral infections for the clinician, CSF data are the most relevant. The use of additional cell lines improves the yield at the cost of increasing the labor and resource required.

Immunodiagnostic techniques for the enteroviruses have been fraught with difficulties resulting from the extreme antigenic diversity among the serotypes. Although a common antigen may exist among the polioviruses and another among the coxsackievirus B types, checkerboard pools of antisera would be required to cover even the most common enteroviral serotypes responsible for human disease. Serologic testing suffers from the same lack of a ubiquitous enteroviral antigen as immunoassays do, requiring, in this case, pools of antigens for testing. Coxsackievirus type B immunoglobulin M serology has the most proven clinical application. It has been found to be advantageous because of shared antigen and early appearance of the immunoglobulin M class of antibodies. Immunoglobulin G serology for the enteroviruses is useful for epidemiologic studies, but of little benefit to the individual patient.

DNA and RNA probes have been used to detect enteroviruses. In Rotbart et al., J. Clin. Microbiol. 20: 1105-1108, (1984), three nucleotide hybridization probes derived from DNA clones of the poliovirus type 1 genome were used in dot hybridization experiments. The probes successfully detected members of each of the major enteroviral subgroups. In Rotbart et al., J. Clin. Microbiol 22: 220-224, (1985), cDNA probes derived from poliovirus 1 and coxsackievirus B3 were used to detect enteroviruses in cerebrospinal fluid reconstruction experiments where an array of enteroviruses were added to cerebrospinal fluid. The viruses were detected by a dot hybridization assay using cDNA probes. Although cDNA probes have been able to detect enteroviruses in cerebrospinal fluid reconstructions, in clinical tests the probes were relatively insensitive in detecting enteroviral infection, Rotbart and Levin, Chapter 15, "Progress Toward the Development of a Pan-Enteroviral Nucleic Acid Probe", in *DNA Probes for Infectious Diseases*, pp. 193–209, 197. In the clinical tests, two thirds of cerebrospinal test fluids that proved positive with tissue culture were missed by the cDNA probes. Single stranded RNA probes (Rotbart et al., Molecular and Cellular Probes 2: 65–73, (1988) can be several times more sensitive than cDNA probes, however, even this improved sensitivity may be too little to routinely detect enteroviruses in cerebrospinal fluid. It is estimated that cerebrospinal fluid from patients with aseptic meningitis due to human enterovirus contains $10^1$–$10^3$ virions per milliliter. The sensitivity of the RNA probes approached this level; nevertheless, the low levels of virus in body fluids preclude the reliable use of the probes for diagnosing picornaviral infection on a routine basis.

There is thus a great need for sensitive methods for detecting picornaviruses in biological fluids and tissues that can be applied to the small amounts of virus often present and that can be quickly performed so that timely diagnosis of infection can be made.

SUMMARY OF THE INVENTION

The present invention provides methods, primers and probes for the detection of picornavirus infections in biological fluids and tissue. In the methods of the invention, at least a portion of picornavirus nucleic acid present in a test sample of a biological fluids or tissue suspected of containing picornavirus is amplified (i.e. multiple copies of the nucleic acid are made) and the amplified picornavirus nucleic acid is then detected. Detection may be accomplished by conventional separation techniques such as gel electrophoresis or by hybridization of at least a portion of a nucleotide probe comprising a nucleotide sequence complementary to the amplified picornaviral nucleic acid. The amplified picornaviral nucleic may also be detected by any suitable combination of detection techniques such as gel electrophoresis followed by hybridization with a nucleic acid probe.

The invention also provides nucleotide primers and probes comprising nucleotode sequences characteristic of picornavirus genomic RNA for use in detecting picornaviruses. Preferred nucleotide probes have the nucleotide sequence 5'-GAAACACGGACACC-CAAAGTA-3' or a nucleotide sequence having substantially the same nucleotide sequence and having substantially the same hybridization activity. The nucleotide probes of the invention may also further comprise a detectable label such as a radiolabel or enzyme label. Preferred nucleotide primers comprise nucleotide sequences selected from the group consisting of 5'-ATTGTCACCATAAGCAGCCA-3', 5'-CCTCCGGCCCCTGAATGCGGCTAAT-3' and nucleotide sequences having substantially the same nucleotide sequence and having substantially the same annealing and priming activities.

The invention further provides kits for detection of picornaviruses in biological fluids and tissues comprising at least one reagent comprising nucleotide primer capable of annealing to and priming for amplification with nucleic acid characteristic of picornaviruses and at least one reagent comprising a nucleotide probe capable of hybridizing with the amplified picornavirus nucleic acid.

The methods of the invention make it possible to detect a wide spectrum of picornaviruses. This is especially useful in clinical practice. Picornavirus infection is often clinically impossible to distinguish from infections due to bacterial pathogens or other viruses, including herpes simplex, for which there are specific therapies. The methods of the invention overcome this problem in diagnosis by providing a rapid, easy to perform method of distinguishing a large group of viral pathogens. The methods of the invention provide means for detecting a wide spectrum of picornaviral serotypes, thus eliminating the need for multiple diagnostic tests. The methods of the invention also reduce delay in beginning treatment if picornavirus infection is present. Infection by most types of this virus family is treated with the same clinical interventions, so such treatment can begin soon after diagnosis and the specific serotype determined at a later time only if indicated ( indications for serotyping are rare and few).

DETAILED DESCRIPTION OF THE INVENTION

The methods of the invention are suitable for detecting picornaviruses. The picornaviruses include polioviruses, coxsackieviruses, echoviruses, enteroviruses and rhinoviruses. A number of picornaviruses have been found to share significant sequence homologies and nucleotide probes and primers having sequences derived from these homologous regions can detect viral types having these regions.

The methods of the invention are performed with viral RNA as the starting material. The RNA is then transcribed into cDNA with reverse transcriptase. This step can be performed as the first round of amplification or can be performed separately. The cDNA is then amplified, preferably using the polymerase chain reaction method, as disclosed in U.S. Pat. Nos. 4,683,195 and 4,683,202, the disclosures of which are specifically incorporated as if fully set forth herein. In the polymerase chain reaction, nucleic acid consisting of two separate complementary strands of equal or unequal length are treated with two oligonucleotide primers under conditions such that for each different sequence being amplified an extension product of each primer is synthesized which is complementary to each nucleic acid strand. Typically, the nucleic acid to be amplified is mixed with the primers, an inducing agent such as DNA polymerase and excess amounts of the nucleotides found in DNA. The primers are selected from bases at both ends of the sequence it is desired to amplify so as to be substantially complementary to different strands of each specific sequence, such that the extension product synthesized from one primer, when it is separated from its complement, can serve as a template for synthesis of the extension product of the other primer. The primer extension products are then separated from the templates on which they were synthesized, usually by heat denaturation, to produce single-stranded molecules. The single-stranded molecules generated and the primers are then treated under conditions such that a primer extension product is synthesized using each of the single strands produced in the previous step as a template. The steps can be conducted sequentially or simultaneously and can be repeated until the desired level of sequence amplification is obtained (see particularly U.S. Pat. No. 4,683,202 at columns 5-12). The starting material for the polymerase chain reaction may be DNA or RNA in purified or nonpurified form, as disclosed in U.S. Pat. No. 4,683,202 at column 5 lines 34-45.

If the original nucleic acid containing the sequence to be amplified is single stranded, its complement is synthesized by adding one or two oligonucleotide primers thereto. If an appropriate single primer is added, a primer extension product is synthesized in the presence of the primer, an inducer or catalyst of the synthesis and the four deoxyribonucleoside triphosphates (i.e., dATP, dCTP, dGTP and TTP). The product will be partially complementary to the single-stranded nucleic acid and will hybridize with the nucleic acid strand to form a duplex of unequal length strands that may then be separated into single strands as described above to produce two single separated complementary strands (see U.S. Pat. No. 4,683,202 at column 7, lines 3-23). The primer extension products are generally formed by a DNA polymerase reaction using nucleotides and the primers as templates. When single stranded RNA is used as the starting material, reverse transcriptase may be used for the first amplification round using the appropriate primers, and further rounds of amplification would utilize DNA polymerase. For the purposes of the methods of the invention, the polymerase chain reaction is allowed to proceed through 15-35 cycles, more preferably 20-30 cycles, of denaturation, reannealling and chain elongation. Other methods of amplification of the nucleic acid of picornaviruses such as cloning or tissue culture may also be suitable in some situations.

The amplified cDNA is then detected by conventional separation techniques such as gel electrophoresis (revealing a characteristic band of 155 nucleotides in length) or by hybridization with a nucleic acid probe.

Primers and probes are selected from regions of the genome of picornaviruses that have substantial or absolute homology with each other. The primers and probes are complementary to these regions so they will hybridize (or anneal) with the corresponding regions of genomic RNA or amplified cDNA. The primers and probe should be selected to be non-overlapping, so that false positives due to hybridization of the primers will be minimized. The primers and probe are preferably at least about nineteen nucleotides long to minimize non-specific hybridization up to about 50 nucleotides in length, more preferably from about nineteen nucleotides to about 30 nucleotides in length. The primers are selected from parts of the viral genomes that are upstream and downstream from the probe. The probe is selected from intervening parts of the genome, so that the probe will detect the amplified cDNA which is characteristic of picornaviruses. The primers are preferably DNA, since they will hybridize with cDNA made with viral RNA as template in the amplification step. The probes of the invention may be DNA or RNA.

The nucleotide sequences of poliovirus types 1, 2 and 3 (as disclosed in Toyoda et al., "Complete Nucleotide Sequences of All Three Poliovirus Serotype Genomes", J. Mol Biol 174: 561-585, (1984), coxsackievirus B1 (as disclosed in Iizuka et al., Virology 156: 64-73, (1987)), coxsackievirus B3 (as disclosed in Lindberg et al., Virology 156: 50-63, (1987)), and coxsackievirus B4 (as disclosed in Jankins et al., J. Gen. Virol. 68: 1835-1848, (1987)) were compared to each other to determine regions of substantial or absolute homology. Sequences showing 100% homology among these 6 serotypes are shown below. These sequences are expected to be characteristic of most picornavirus serotypes, with only small changes in base sequence among serotypes that will not substantially reduce the specificity or sensitivity of the methods of the invention.

PV¹, PV², PV³, CB¹, CB³, CB⁴

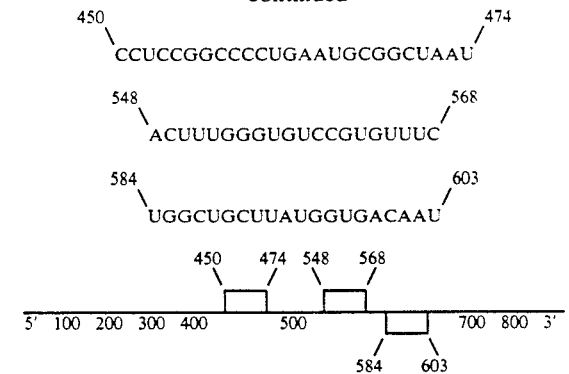

Primer 2 anneals at about 450-474 and participates in the polymerase chain reaction. Primer 1 anneals at about 584-603 and initiates reverse transcription in the first amplification step. Primer 1 then participates in the polymerase chain reaction. The probe binds at about 548-568.

Preferred primers have the following nucleotide sequences

Primer 1- 5'-ATTGTCACCATAAGCAGCCA-3' (Anti-sense with respect to viral genomic RNA)

Primer 2- 5'-CCTCCGGCCCCTGAATGCGG-CTAAT-3' (Sense with respect to viral genomic RNA)

The nucleotide sequence of the primers can be varied by moving in the 5' or 3' directions with reduced homology to the six sequenced picornaviruses.

Preferred nucleotide probes have the following sequence—

Probe-5'-GAAACACGGACACCCAAAGTA-3' (Anti-sense with respect to viral genomic RNA)

Subsets having fewer nucleotide bases, nucleotide sequences shifted 5' or 3' on the viral genome, derivatives that add nucleotide bases not derived from picornaviruses and mutations that change the base sequence of the nucleotide sequences set forth above, which do not substantially detract from the ability of the sequence to hybridize with cDNA from picornavirus RNA are also suitable for use in the invention.

The nucleic acid sequences useful in the nucleotide probes and primers of the invention are readily prepared by any conventional method such as organic synthesis or recombinant DNA techniques. However, the sequences as described herein are particularly amenable to organic synthesis using techniques known in the art, such as techniques employing a nucleic acid synthesizer and commercially available reagents. Methods of chemically synthesizing the probes and primers of the invention are well known in the art; suitable methods can be found in U.S. Pat. No. 4,683,202 and Rotbart et al., J. Clin. Microbiol. 26: 2669-2671, (December, 1988).

The nucleotide probes of the invention are preferably detectably labeled to signal hybridization to the amplified cDNA that is characteristic of picornaviruses. Suitable detectable labels include radiographic, chemical, antibodies and antigens, biotin, electron dense compounds, or light scattering particles. Suitable methods for detecting such labels are scintillation counting, autoradiography, fluorescence measurement, light emission measurement or microscopy. Many of these labels and methods of detecting them are well known in the art and are commercially available. For example, if the detectable label is an enzyme, such as horseradish peroxidase, a detectable signal can be generated by the addition of a chromogenic enzyme substrate, such as Nitro Tetrazolium Blue which is then detected by visual inspection or by spectrophotometric means.

The detectable label may be attached to the probe by any convenient method such as nick translation, Rigby et al., J. Mol. Biol. 113: 237-251, (1977), or the addition of an oligonucleotide tail, Ruth, J. L., DNA 4: 123-128, (1984) and Ruth et al., DNA 4: 93-97, (1985) to which the detectable label attached.

The methods of the invention are suitable for use with many types of biological tissues, particularly cerebrospinal fluid, serum, urine, biopsy and autopsy tissues and including fixed pathological specimens. The lability of free RNA in cerebrospinal fluid makes the preservation of intact virions important. Addition of formaldehyde or another RNase inhibitor such as RNasin, immediately after collection of the specimen from the patient will protect any RNA which becomes exposed by viral capsid opening during transport to the laboratory, as well as during the subsequent testing.

The kits for detection of picornaviruses include reagents comprising primers and probe and, where needed, at least one reagent comprising means for detecting the probe, supplied in separate containers. The primer reagents are preferably supplied in separate containers, since the downstream primer will be used in the initial reverse transcriptase step that produces cDNA from the viral RNA. The probe is preferably supplied with a detectable label attached. The reagent comprising means for detecting the probe will be coordinated with the detectable label so that a detection system is formed. For example, if the detectable label is an enzyme, the reagent comprising means for detecting the probe will contain substrate for the enzyme. However, if the detectable label is a radiolabel and autoradiography is the method selected for detecting the label, there is no need for a detecting reagent and it would be omitted from the kit.

EXAMPLE 1

Eleven types of enteroviruses, polioviruses 1 and 3 (PV1 and PV3), coxsackieviruses B1, B6, A9 and A16 (CB1, CB6, CA9 and CA16), and Echoviruses 2, 4, 6, 11 and 22 (E2, E4, E6, E11, and E22) were obtained from the American Type Culture Collection, Rockville, Md. For three of the types, PV1, PV3 and CB1, the full genomic sequences have been reported. The genomic sequences of the remaining eight enteroviruses have not been reported. Each viral type was individually added as whole virions to saline or cerebrospinal fluid. 1 μl RNasin (from stock of 40 μ/μl) per 100 μl of specimen fluid was added to inhibit RNA degradation.

Viral RNA was extracted by adding sodium dodecyl sulfate (SDS) to a final concentration of 0.5%. Then 1 volume phenol:chloroform was added. The mixture was then spun in an Eppendorf centrifuge for 5 minutes at room temperature. The aqueous phase was removed to a new tube. The organic phase was back extracted by adding an equal volume of: 10 mM Tris HCl pH 7.5, 100 mM NaCl, 1 mM EDTA, and 0.5% SDS. This was spun for 5 minutes at room temperature in an Eppendorf centrifuge and the aqueous phase was removed and added to the previously collected aqueous phase. $NH_4$ acetate was added to the aqueous phase to a final concentration of 2M and 2.5 volumes of cold ETOH were then added. The aqueous phase was stored at $-20°$ overnight; however this step can be shortened to less than one hour if results are desired sooner. The aqueous phase was then spun at 4° for 30 minutes in an Eppendorf centrifuge and the ethanol was carefully poured off. The extracted RNA precipitate remaining in the tubes was allowed to air dry for one to two hours.

The extracted RNA was then amplified using a polymerase chain reaction kit (Cetus Corporation, Emeryville, Calif.), according to the following method. Because RNA was the starting material, the first round of amplification was done with reverse transcriptase. For each test sample and control the following reagents and amounts were used:

| | | |
|---|---|---|
| 1 ul | RNasin (40 u/ul) | |
| 2 ul | 5 × reverse transcription buffer | 250 mM TRIS-Cl 8.3 |
| | | 15 mM $MgCl_2$ |
| | | 350 mM KCl |
| | | 50 mM DTT |
| 1 ul | ATP 10 mM | |
| 1 ul | CTP 10 mM | |
| 1 ul | GTP 10 mM | |
| 1 ul | TTP 10 mM | |
| 2 ul | DEPC $H_2O$ | |

The precipitate pellet was resuspended in 9 ul of the above mix and each resuspended specimen was then transferred to a siliconized 500 ul microtube. To this mixture was added sequentially 1 ul downstream primer (10 pmol/ul), and 1 ul avian reverse transcriptase (5 u/ul). The mixture was then overlayed with 100 ul mineral oil and incubated for 90 minutes at 37° C.

The extracted RNA was then amplified using the polymerase chain reaction method. The following reaction mixture was added to each test sample:

| | | |
|---|---|---|
| 10 ul double distilled $H_2O$ | | |
| 4 ul 10 × PCR buffer | 560 mM KCl | |
| | 100 mM TRIS-Cl pH 8.3 | |
| | 15 mM $MgCl_2$ | |
| | 0.1% w/v gelatin | |
| 6.5 ul diluted mix of DNTP's | 125 ul | dATP 10 mM |
| | 125 ul | dCTP 10 mM |
| | 125 ul | cGTP 10 mM |
| | 125 ul | TTP 10 mM |
| | 500 ul | double distilled sterile water |
| | 1,000 ul | |
| 4 ul downstream primer (10 pmol/ul) | | |
| 4 ul upstream primer (10 pmol/ul) | | |
| 0.5 ul TAQ1 polymerase | | |

The phage control (from the polymerase chain reaction kit) was prepared in a siliconized tube as follows, according to the manufacturer's instructions:

| | |
|---|---|
| 53.5 ul | double distilled sterile water |
| 10 ul | 10 × PCR reaction buffer |
| 16 ul | diluted dNTP mix (see above) |
| 5 ul | control primer #1 |
| 5 ul | control primer #2 |
| 10 ul | control template diluted $10^{-1}$ |
| 100 ul | |

The test samples and control were then overlayed with 100 ul mineral oil. The polymerase chain reaction cycles were run by hand in heat blocks with water in the wells. Twenty-seven cycles were completed on the following schedule:

| First | 95° | 5 minutes |
| --- | --- | --- |
| | 37° | |
| | 72° | 2 minutes each - 25 cycles |
| | 95° | |
| Last | 72° | for 9 minutes |

The test samples and control were refrigerated for later analysis (gel electrophoresis, slot blot hybrization).

A. Agarose gel electrophoresis

One-eighth to one-fourth (5-10 ul) of the polymerase chain reaction (PCR) reaction mixture is added to a dye-containing "stop buffer" (final concentration 10% glycerol, 50 mM EDTA, 0.1% bromphenol blue) and loaded onto a "mini-gel" consisting of 3% NuSieve agarose (FMC Corporation, Philadelphia, Pa.) and 0.5% Ultrapure electrophoresis grade agarose (BRL Products, Gaithersburg, Md.). This combination of agarose was found to give the greatest resolution of amplification product in the size range required. A reference sizing "ladder" of known fragment lengths of control DNA is run with each mini-gel. A putative "positive" specimen is one which produces a distinct band at exactly 155 bases in length (the amplified product = primers of 25 and 20 bases incorporated onto the intervening segment of 110 bases). Confirmation of positives is by slot blot hybridization.

B. Preparation of Primers and Radiolabeled Probes

Primers having the following sequences

Primer 1- 5'-ATTGTCACCATAAGCAGCCA-3' (Anti-sense with respect to viral genomic RNA) and Primer 2- 5'-CCTCCGGCCCCTGAATGCGG-CTAAT-3' (Sense with respect to viral genomic RNA) for use in the polymerase chain reaction were prepared according to the method of Rotbart et al., J. Clin. Microbiol. 26: 2669-2671, (December, 1988), with a DNA synthesizer (Applied Biosystems).

DNA probes having the sequence 5'-GAAACACG-GACACCCAAAGTA-3' were prepared according to the method of Rotbart et al., J. Clin. Microbiol. 26: 2669-2671, (December, 1988) with a DNA synthesizer (Applied Biosystems). $^{32}$P labeling of the oligomers was done by standard kinase end labeling according to the method of Maniatis et al., *Molecular cloning: a laboratory manual*, Cold Spring Harbor Laboratory, Cold Spring Harbor, N.Y., pp. 117-127. The synthesized oligomers were purified with C-18 Sep-pak cartridges (Waters Associates, Inc., Milford Mass.).

C. Slot Blot Hybridization

Another aliquot (1-10 ul) of the PCR reaction mixture is brought to 100 ul volume with phosphate-buffered saline. To that is added 60 ul of 20× SSC (1× SSC is 0.15M NaCl plus 0.015M sodium citrate, pH 7.0) and 40 ul of 37% formaldehyde. This mixture is then heated to 60° C. for 15 minutes. This treatment optimizes rentention of target nucleic acid on filter paper for subsequent hybridization. After heating, the specimen is then applied to GeneScreen Plus nylon membrane filters (Dupont, NEN Research Products) through a slot blot apparatus (Schleicher and Schuell, Inc., Keene, N.H.). The filter is allowed to air dry, UV irradiated for 15 minutes to improve retention of nucleic acid, and inserted into a plastic baggie for hybridization. A prehybridization step consists of incubating the filter in a solution of 5× SSC, 1% sodium dodecyl sulfate (SDS), and 5× Denhart's solution (Denhart, Biochem. Biophys. Res. Commun. 23: 641-646, (1966)) for 15 minutes at 55° C. For hybridization, the baggie is opened, and 5 mM radioactive (non-radioactive probe can be used at this step as well) probe is added—the probe is specific for part of the 110 base intervening sequence and does not overlap with the primers. Following a 30 minutes hybridization at 55° C., three 5 minute washes in a mixture of 1× SSC and 1% SDS at 55° C. are performed. The filter is allowed to partially air dry and is then exposed to XAR-5 Kodak film for autoradiography. The exposure length can be as short as 5 minutes, but often is best at 2-4 hours.

EXAMPLE 2

Poliovirus 3, coxsackieviruses B6 and A9, echoviruses E2, E6 and E22; and rhinoviruses 2 and 14, lambda phage control DNA were tested according to the method in Example 1. Slot blot hybridization of multiple amplified enteroviral RNAs showed positive signals with poliovirus 3, coxsackieviruses B6 and A9, echoviruses E2, E6 and E22; and rhinoviruses 2 and 14. The lambda phage control DNA gave no hybridization signal.

EXAMPLE 3

Slot blot hybridization of cerebrospinal fluid (CSF) specimens from a patient with chronic enterovirus (echovirus 11) infection due to an underlying immunodeficiency. Following treatment with intravenous and intrathecal gammaglobulin, the patient's CSF became "sterile", i.e., no virus could be grown, but the patient was still symptomatic, indicating ongoing infection. This was confirmed by testing specimens of the patients CSF using the method in Example 1, in which serial specimens were shown to be positive for echovirus 11 RNA, including specimens which were culture positive (1 specimen) and those which were culture negative (6 specimens). Echovirus 11 controls consisted of the known virus added in the laboratory to either phosphate buffered saline (PBS) or normal CSF from a patient without infection.

I claim:

1. A nucleotide probe for the detection of picornaviruses consisting essentially of the nucleotide sequence 5'-GAAACACGGACACCCAAAGTA-3' or a nucleotide sequence having substantially the same nucleotide sequence and having substantially the same hybridization activity.

2. The nucleotide probe of claim 1 wherein said probe is detectably labelled.

3. The nucleotide probe of claim 2 wherein said detectable label is a radiolabel.

4. The nucleotide probe of claim 2 wherein said detectable label is an enzyme.

5. A nucleotide primer for use in detecting picornaviruses consisting essentially of a nucleotide sequence selected from the group consisting of

5'-ATTGTCACCATAAGCAGCCA-3'

5'-CCTCCGGCCCCTGAATGCGGCTAAT-3' an nucleotide sequences having substantially the same nucleotide sequence and having substantially the same hybridization activity.

6. The nucleotide primer of claim 5 wherein said nucleotide sequence is

5'-ATTGTCACCATAAGCAGCCA-3'

7. The nucleotide sequence of claim 5 where in said nucleotide sequence is

5'-CCTCCGGCCCCTGAATGCGGCTAAT-3'

* * * * *